US00RE36132E

United States Patent [19]

Heacox

[11] E Patent Number: Re. 36,132

[45] Reissued Date of Patent: Mar. 9, 1999

[54] THREE ENVELOPE PACKAGE FOR STERILE SPECIMENS

[75] Inventor: Albert E. Heacox, Marietta, Ga.

[73] Assignee: CryoLife, Inc., Kennesaw, Ga.

[21] Appl. No.: 630,464

[22] Filed: Apr. 10, 1996

Related U.S. Patent Documents

Reissue of:

[64] Patent No.: 5,257,692
Issued: Nov. 2, 1993
Appl. No.: 730,356
Filed: Jul. 15, 1991

U.S. Applications:

[63] Continuation of Ser. No. 395,297, Aug. 17, 1989, Pat. No. 5,031,762, which is a continuation-in-part of Ser. No. 105,220, Oct. 7, 1987, abandoned.

[51] Int. Cl.[6] ..... B65D 81/18

[52] U.S. Cl. ..... 206/210; 206/438; 206/484

[58] Field of Search ..... 206/63.3, 63.5, 206/205, 210, 213.1, 438–441, 484; 62/55.5, 371, 372, 457.9; 220/901; 604/289, 290; 623/11, 15, 66

[56] References Cited

U.S. PATENT DOCUMENTS

| | | | |
|---|---|---|---|
| 3,143,209 | 8/1964 | Turiansky | 206/63.3 |
| 3,189,174 | 6/1965 | Cormack | 206/63.3 |
| 3,202,273 | 8/1965 | Riall | 206/63.3 |
| 3,256,981 | 6/1966 | Kurtz | 206/63.3 |
| 3,761,013 | 9/1973 | Schuster . | |
| 3,815,315 | 6/1974 | Glick | 206/63.3 |
| 3,819,106 | 6/1974 | Schuster . | |
| 3,926,309 | 12/1975 | Center | 206/364 |
| 3,942,529 | 3/1976 | Waage | 128/272 |
| 4,482,053 | 11/1984 | Alpern et al. | 206/439 |
| 4,597,764 | 7/1986 | Klatt | 206/63.3 |

OTHER PUBLICATIONS

Chemical Tests on Kapton/Rep Laminate Film Type 300F021, no date.

Kapton Product Brochure, Mar. 1988.

"The Use of Aortic Valve Homografts for Aortic Replacement," Wallace, R.B., Biological Tissue in Heart Valve Replacement, pp. 333–335, 1972.

"The Viable Cryopreserved Allograft Aortic Valve," O'Brien, M.F. et al., Journal of Cardiac Surgery, vol. 2 No. 1, suppl., Mar. 1987.

"A Fresh, Viable Human Heart Valve Bank: Sterilization, Sterility, Testing and Cryogenic Preservation," Angell, J.D. et al., Transplant Proc. 8(2) [suppl.]: 139–147, 1976.

"Long-term Follow-up of Viable Frozen Aortic Homografts," Angell, W.W. et al., Journal of Thoracic and Cardiovascular Surgery, 93:815–822, 1987.

*Primary Examiner*—Jim Foster
*Attorney, Agent, or Firm*—Brinks Hofer Gilson & Lione

[57] ABSTRACT

A three-envelope package for preserving tissue specimens or other sterile objects. A sterile tissue sample is sealed within an innermost envelope sterile inside and out. The innermost envelope is sealed within the sterile interior of an intermediate envelope equipped with a peel-back seal for subsequent opening. Both the inside and the outside of the intermediate envelope are sterile. The intermediate envelope is sealed within the sterile interior of an outermost envelope, made of foil or another substance impermeable to a storage medium, such as liquid nitrogen. The outermost envelope provides complete impermeability to liquid nitrogen, eliminating the possibility of nitrogen seepage through the peel-back seal of the intermediate envelope. When the envelope package is removed from storage, the intermediate envelope is removed from the outermost envelope and can be opened in an assumed non-sterile environment, without contaminating the innermost envelope or the tissue specimen therein.

6 Claims, 2 Drawing Sheets

THREE ENVELOPE PACKAGE FOR STERILE SPECIMENS

Matter enclosed in heavy brackets [ ] appears in the original patent but forms no part of this reissue specification; matter printed in italics indicates the additions made by reissue.

This is a continuation of application Ser. No. 395,297 filed Aug. 17, 1989, now U.S. Pat. No. 5,031,762, which is a continuation-in-part of application Ser. No. 105,220 filed Oct. 7, 1987, abandoned.

TECHNICAL FIELD

The present invention relates in general to packaging for sterile specimens, and more particularly relates to a package for storing a sterile transplant specimen in a preserving medium and maintaining sterility when subsequently removing the specimens from the package.

BACKGROUND OF THE INVENTION

There are presently available various kinds of packaging for sterile specimens. The sterile specimens may be biological, marine, or agricultural specimens stored for analysis in a laboratory. The sterile specimen may also be human or animal tissue for use in transplants.

Human tissue transplant operations have become commonplace in recent times. The success of these transplant operations has created a high demand for the human tissue. However, it is often difficult to find fresh donor tissue for immediate transplant to a recipient. Donor tissue must match the recipient's tissue as closely as possible, to minimize the risk of tissue rejection by the recipient's immune system, and for that reason homografts are preferred; heart valves and blood vessels are two examples of human tissue currently used for human homografts. The tissue is preferably preserved and stored for later implant so that a supply of tissue is on hand independently of immediate donor availability.

Human and animal tissue is preferably cryopreserved for storage beyond a few hours. The tissue, after excision from the donor and suitable treatment as known to those skilled in the art, is stored in a sterile package impermeable to bacteria and then frozen, after which the frozen tissue is stored at a low temperature for relatively long-term preservation. Because the low temperatures required for effective cryopreservation are not attainable by economically-feasible mechanical refrigeration equipment, the packaged tissue specimens are stored by immersion in liquid nitrogen to maintain the cryopreserved tissue viable throughout storage. It is, therefore, important that the storage package be impermeable to liquid nitrogen. When a suitable recipient is found for the tissue, the storage package is removed from the liquid nitrogen storage facility. The tissue is then thawed and removed from its storage package immediately before implant in the recipient.

The tissue must be kept sterile during removal from the storage package before implanting in the recipient. This is not a trivial requirement, as the exterior surface of the storage package is nonsterile or is presumed as such. The sterile packages known in the prior art are inadequate for storing cryopreserved human or animal tissue specimens, because these packages cannot insure the sterility of the specimen when the package is stored in an unsterile coolant medium such as liquid nitrogen. Packaging material impermeable to liquid nitrogen is well known, metallic foil being one example, but simply making the prior art packaging out of material impermeable to liquid nitrogen does not solve the problems of sterility. Because the outer surface of such an envelope is unsterile, there is a risk of contamination of the specimen when the envelope is cut open and the specimen is pulled out of the envelope.

Foil envelopes or pouches with a peel-back opening feature have been proposed as a solution to the foregoing problem. A peel-back opening allows an envelope to be opened by pulling apart the two sides of the envelope, so that the contents are exposed and can be removed without contacting the outer surface of the envelope. However, the outer surface of any single-envelope package is always considered unsterile. A further problem with a single envelope package is that an envelope with a peel-back opening feature is not impermeable to liquid nitrogen. Since a single-envelope package for storing specimens in liquid nitrogen cannot have a peel-back opening, the envelope must be cut open to remove the specimen. There is then a substantial risk that the specimen will make actual physical contact with the unsterile outer surface or opening of the envelope and become contaminated.

Various double-envelope packages for storing sterile specimens have been proposed. A typical double envelope package for storing specimens is also inadequate for insuring sterility of a cryopreserved specimen. A typical double envelope package is made of a sterile inner envelope that contains the specimen, and this inner envelope is stored in an outer envelope impermeable to liquid nitrogen. When the outer envelope is cut open and the inner envelope is removed, there is a substantial risk that the sterile outer surface of the inner envelope will become contaminated from contact with the unsterile outer surface of the outer envelope. Likewise, when the sterile specimen is removed from the inner envelope, there is some risk that the specimen will be contaminated by the presumed-unsterile outer surface of the inner envelope. Making the inner bag with a peel-back opening in a two-envelope package does not solve the problem of sterility. The tissue specimen is stored in a liquid medium in the inner envelope. If the inner envelope is opened by peeling off part of the inner envelope, the liquid will pour uncontrollably out of the inner envelope, and contact the outside surface of the inner envelope, causing inconvenience and a further risk of contamination to the specimen.

Therefore, there is a need for a package for storing sterile tissue specimens in a coolant medium such as liquid nitrogen and maintaining the sterility of the tissue specimen when the specimen is removed from the packaging.

SUMMARY OF THE INVENTION

The present invention solves the above-described problems in the prior art by providing a three-envelope package for storing sterile specimens. Generally described, the present invention is comprised of three envelopes: an inner envelope, an intermediate envelope, and an outer envelope. The inner envelope is made of a material completely impermeable to bacteria, and the sterile tissue specimen is stored in the inner envelope. The inner envelope is sterile inside and out, when a tissue specimen is deposited therein.

The inner envelope is then stored in the intermediate envelope, also made of a material impermeable to bacteria. The intermediate envelope is also sterilized inside and out, when the inner envelope is stored therein. In the preferred embodiment of this invention, the intermediate envelope is made with a peel-back flap that allows the intermediate envelope to be opened by pulling the two sides of the envelope apart, thereby exposing the contents of the inner envelope.

The intermediate envelope is stored in the outer envelope. The outer envelope is made of a material completely impermeable both to liquid nitrogen and bacteria. The outer envelope is sterile on the inside when stored but is not sterile on the outside when stored, because the outer surface of the outer envelope contacts an unsterile universe including the cryogenic coolant medium.

The novel construction of the present invention insures the sterility of the tissue specimen as the specimen is removed from the package. When the tissue specimen is needed, the package containing the sterile specimen is removed from the coolant medium and the tissue specimen is thawed. The outer envelope is then cut open, and the intermediate envelope is pulled from the outer envelope and the outer envelope is discarded. It is possible that the outer surface of the intermediate envelope is contaminated by contact with the unsterile cut edge of the outer envelope as the intermediate envelope is removed, and in any case the outer surface of the intermediate envelope is treated as if it were contaminated. Although the outer surface of the intermediate envelope is presumed unsterile, the inner envelope can remain sterile while being removed from the intermediate envelope. The peel-back flap of the intermediate envelope is pulled, thereby pulling apart the two sides of the intermediate envelope and exposing the inner envelope. Next, the inner envelope is lifted from the intermediate envelope by a sterile instrument so that the inner envelope does not contact the peeled-back unsterile outer surface of the intermediate envelope. The outer surface of the inner envelope thus remains sterile after the inner envelope is removed from the intermediate envelope. The intermediate envelope is then discarded and the sterile inner envelope is introduced to a sterile environment. The tissue specimen is there removed from the inner envelope with no risk of contamination from contact with the outer surface of the intermediate envelope.

Therefore, it is an object of the present invention to provide an improved package for cryopreserving a tissue specimen until the tissue specimen can be implanted in a recipient.

It is a further object of the present invention to provide a package for storing sterile tissue specimens in a cooling medium such as liquid nitrogen.

It is a another object of the invention to provide a package for storing tissue specimens whereby the tissue specimen can be removed therefrom in a sterile condition.

Other objects, features and advantages will become apparent from reading the following specifications in conjunction with the accompanying drawings.

DETAILED DESCRIPTION OF PREFERRED EMBODIMENT

Figure 1:
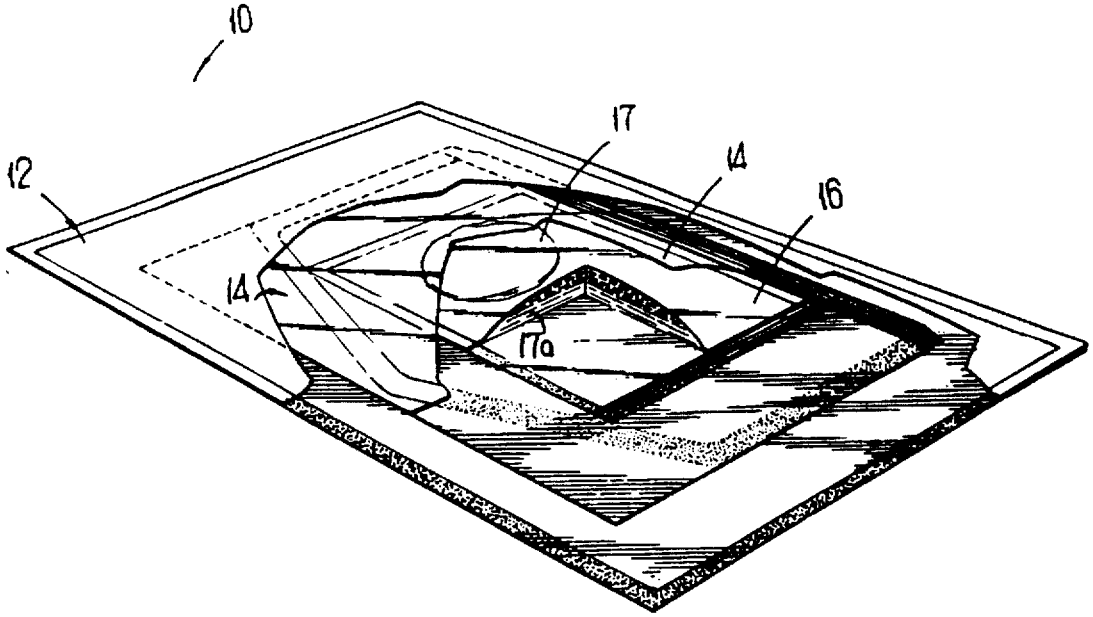
FIG. 1 is a pictorial view, partially broken away for illustrative purposes, showing a package according to a preferred embodiment of the present invention.
Figure 2:
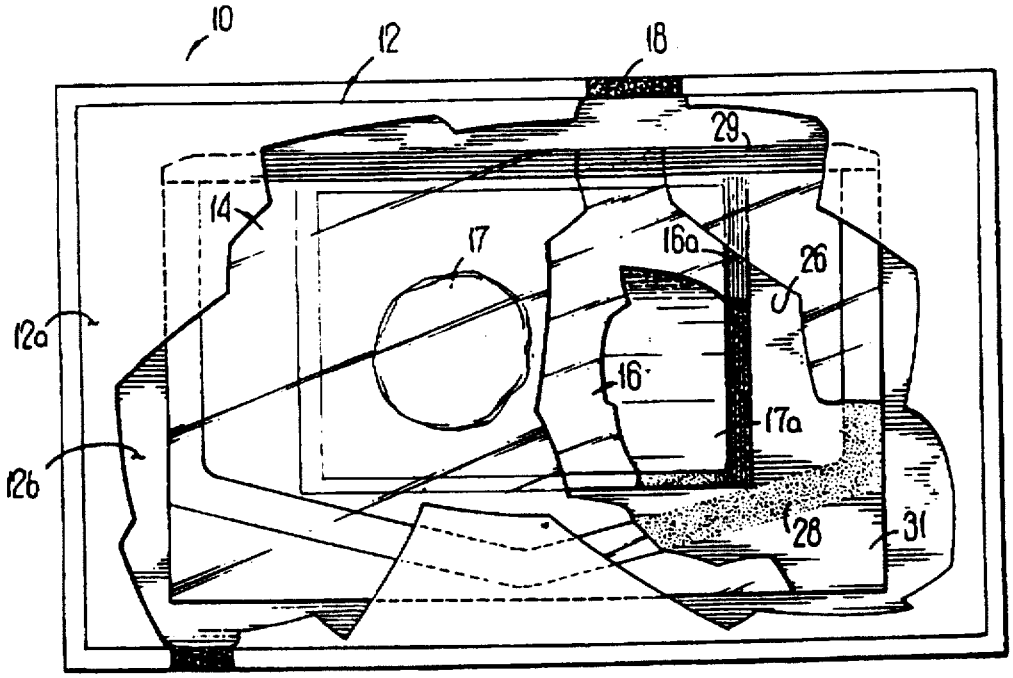
FIG. 2 is a plan view, also partially broken away, showing the package of FIG. 1.

Referring first to FIGS. 1 and 2, there is shown generally at 10 an envelope package including three individual envelopes or pouches. These envelopes are the outermost envelope 12, an intermediate envelope 14 contained immediately within the outermost envelope, and an innermost envelope 16 received within the intermediate envelope. The tissue specimen (generally at 17) is contained within only the innermost envelope 16 in the present embodiment of the invention, and it will be understood that the innermost envelope may also contain a suitable liquid medium (17a) for preserving the viability of the tissue specimen. Furthermore, although the disclosed embodiment is discussed as a sterile means for storing and substantially utilizing a cryopreserved specimen of human or animal tissue, that specific application is not intended to limit the utility of the present invention.

The outermost envelope 12 provides the dual functions of isolating its sterile interior from bacteria, and of providing an impermeable barrier to the cryogenic atmosphere (irrespective of sterility) in which the envelope is kept. Liquid nitrogen comprises the particular cryogenic atmosphere of concern for the envelope package 10 of the preferred embodiment, and so the outermost envelope 12 must be impervious to liquid nitrogen. A metallic foil, such as aluminum foil or the like, is a preferred material for fabricating the outermost envelope 12.

The outermost envelope is fabricated from two foil panels 12a and a 12b (FIG. 2) of equal dimensions, overlaying each other and enclosing the intermediate envelope 14. The interior of the outermost envelope 12 is sterilized before receiving the intermediate envelope 14. The peripheral edges 18 of the outermost envelope 12 are then welded shut along the aligned 19 by heat sealing or another appropriate sealing technique which makes the outermost envelope impervious to bacteria and to penetration by the liquid nitrogen in which the envelope package 10 is then placed.

The innermost envelope 16 receives the sterile tissue specimen 17 and, typically, a liquid medium (17a) which bathes the tissue specimen. The innermost envelope 16, while in the envelope package 10, is not exposed to liquid nitrogen, nor to an unsterile condition, and so the innermost envelope is preferably a polyester bag of sufficient size to contain the tissue specimen and any supporting liquid medium. The innermost envelope is sterile inside and out, and is sealed shut at one end 16a by heat sealing or the like after the tissue specimen and any liquid medium are in place within the innermost envelope.

The intermediate envelope 14 is preferably of peel-back construction, to facilitate subsequent opening of that envelope without subjecting the innermost envelope 16 contained within the intermediate envelope, to possible contamination on the outer surface of the intermediate envelope. However, the intermediate envelope 14 is protected by the outermost envelope 12 against exposure to the liquid nitrogen storage medium, and so the possibility of liquid nitrogen seeping through the peel-back seal of the intermediate envelope is eliminated.

Figure 3:
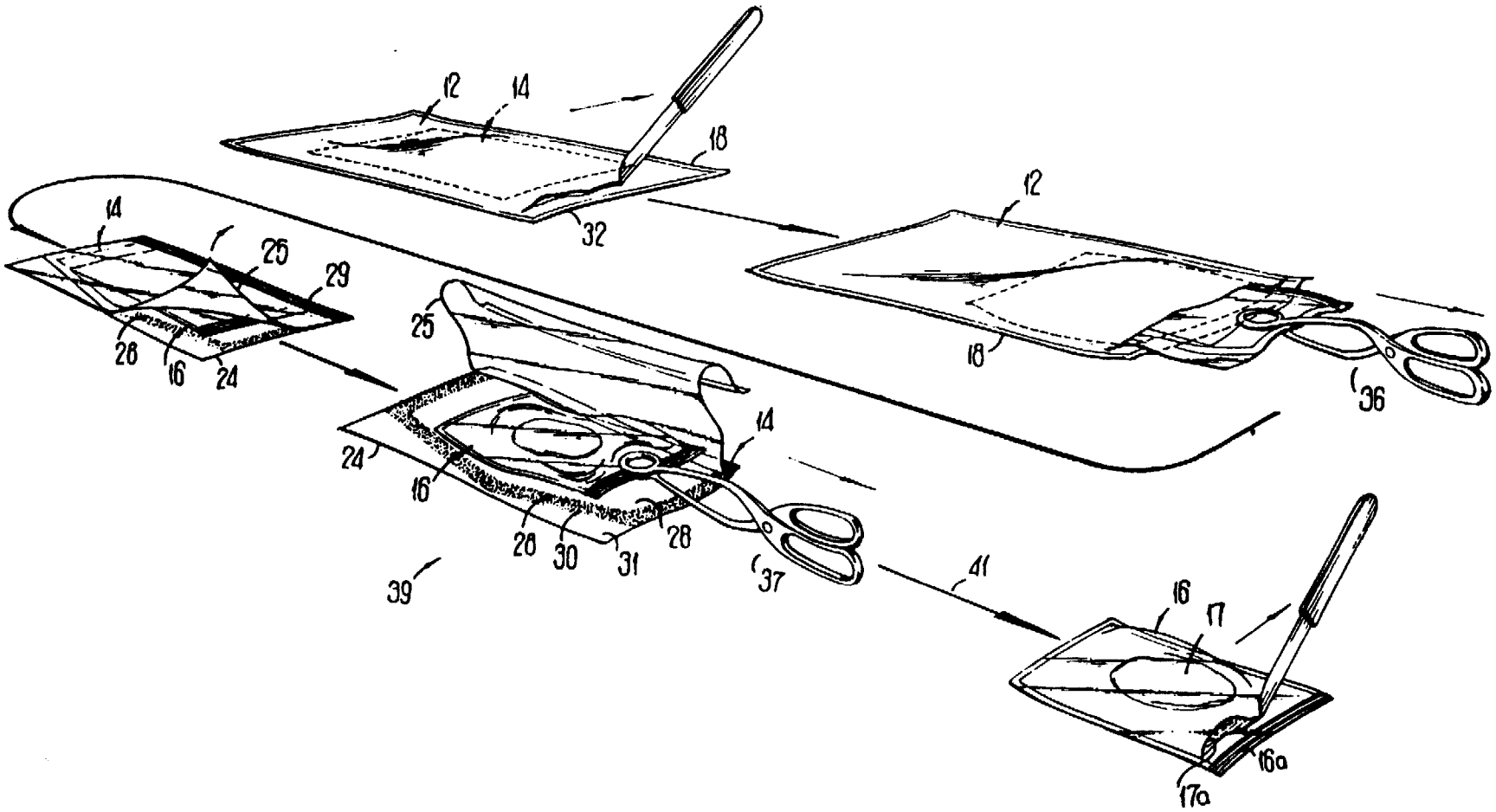
FIG. 3 is a pictorial view illustrating the stages of opening the package shown in FIGS. 1 and 2.

Details of the intermediate envelope 14 are best seen in FIG. 3. The intermediate envelope 14 is of two-piece construction, including a lower layer 24 sandwiched beneath an upper layer 25. The upper and lower layers are preferably rectangular sheets of thin flexible material such as foil or polyester, as is known to those skilled in the art. Confronting peripheral portions of the facing surfaces on the layers 24 and 25 are sealed together as at the seal line 28, and this seal line preferably extends on three sides of the intermediate envelope 14. The seal 28 is a peel-back seal of known construction, in which the confronting surfaces of the lower layer 24 and the upper layer 25 are tack-sealed together by heating or the like, forming an airtight seal impervious to the passage of bacteria or other contaminants. The fourth side 29 of the intermediate envelope 14 is welded together in a relatively permanent seal, and the fourth side also is impervious to bacteria or other contaminants. The seal 28 and fourth side 29 thus define an interior region 26 within the intermediate envelope 14, and this interior region is of sufficient dimension to receive the aforementioned innermost envelope 16 as illustrated in FIG. 4. Both the inside and outside of the intermediate envelope 14 are sterilized.

A preferred construction of the intermediate envelope 14 has one of the layers 24 and 25, for example, the upper layer 25, made of a transparent polyester sheet, and the other layer made of foil, the two layers being heat-sealed or otherwise interconnected along three sides to form the peel-back seal 28. The peel-back seal 28 preferably follows a diagonal path 30 across at least one corner of the intermediate envelope 14, leaving the outermost corner 31 unsealed to facilitate grasping and opening the peel-back seal. The use of dissimilar materials, such as foil and vinyl, for the layers 24 and 25 facilitates forming a seal 28 having the desired peel-back characteristics necessary for opening the envelope package as described below. Inasmuch as the outermost envelope 12 is a barrier to liquid nitrogen, the intermediate envelope 14 is never subjected to liquid nitrogen and the permeability of peel-back seals to liquid nitrogen is not a problem with the present envelope package 10.

The package described herein further serves to protect the cryogenically preserved transplantable tissue contained in the innermost envelope. To facilitate the cryogenic preservation of the transplantable tissue contained in the package described herein, the package should be made of material which is suitable for exposure to extremely low temperatures, e.g., −196 degrees C. to elevated temperatures, e.g., +37 degrees C., such as are observed and utilized in the preparation of cryogenically preserved tissue for transplant into a patient in need of such treatment. The envelope material should withstand wide, rapid, extreme freeze-thaw temperature changes without cracking, be chemically inert and enhance or preserve the tissue to improve tissue viability upon transplant. Table I shows a list of commonly available materials and their brittleness temperatures.

TABLE I

LIST OF COMMONLY USED PLASTICS

| Resin | Brittleness Temp (°F./°C. |
|---|---|
| LDPE* | −148/−100 |
| HDPE* | −148/−100 |
| XLPE | −180/−118 |
| PP | 32/0 |
| PA | −40/−40 |
| PMP | 68/20 |
| PS | −148/−100 |
| PVC | −22/−30 |
| ACL | — |
| NYL* | 32/0 |
| PC | −211/−135 |
| PSF | −148/−100 |
| FEP* | −454/−270 |
| ETFE/ECTFE | −157/−105 |

TABLE I-continued

LIST OF COMMONLY USED PLASTICS

| Resin | Brittleness Temp (°F./°C. |
|---|---|
| PFA | −454/−270 |
| PUR | −94/−70 |

LEGEND
LDPE: Low-density polyethylene
HDPE: High-density polyethylene
XLPE: Cross-linked, high-density polyethylene
PP: Polypropylene
PA: Polyallomer
PMP: Polymethylpentene
PMMA: Polymethyl methacrylate
PVC: Polyvinyl chloride
ACL: Acetal (polyoxymethylene)
NYL: Nylon (polyamide)
PC: Polycarbonate
PSF: Polysulfone
TFE: Teflon TFE (tetrafluoroethylene)
FEP: Teflon FEP (fluorinated ethylene polypropylene)
ETFE: Tefzel ETFE (ethylene-tetrafluoroethylene)
ECTFE: Halar ECTFE (ethylene-chlorotrifluoroethylene copolymer)
PFA: Teflon PFA (perfluoroalkoyl)
PUR: Polyurethane
PVDF: Polyvinylidene fluoride
PS: Polystyrene

*Materials tested in this study

At temperatures near or below the brittleness temperature, these materials become fragile. An example of material which is not generally suitable for use in the envelope described herein is ordinary polyethylene, which does not adequately protect the tissue upon thawing. The tissue envelope is easily damaged during freezing, thawing, and shipping, and the tissue may develop cracks upon thawing rendering the tissue unacceptable for transplant purposes.

A three-part test has been developed to select materials which are suitable for cryogenic packaging. Part A is a general screening test whereby a sample of the test material is placed into liquid nitrogen (−196 degrees C.) to expose the material to ultracold temperatures. The material is then removed from the liquid nitrogen, and placed into a warm bath until the temperature equilibrates at 37 degrees C. This simulates actual treatment conditions during preparation for transplant surgery.

Part B of the screening procedure utilizes a 100 ml quantity of water cryogenically frozen in an envelope comprised of the test material. After freezing, the package is removed from liquid nitrogen and dropped immediately from a height of 40 to 45 inches. The package is visually inspected for damage to the test material.

Part C of the test is identical to part B, except that the test material and water contained therein are first cryogenically frozen and then warmed to 37° C. The samples are then dropped from a height of 36 to 40 inches and examined for damage.

The test results are presented below in table II.

TABLE II

RESULTS

| Test Materials | A | B | C |
|---|---|---|---|
| Polymide/FEP | 3 | 3 | 3 |
| Foil/Polyester/Polyethylene | 3 | 1–2 | 2 |

TABLE II-continued

| Test Materials | RESULTS A | B | C |
|---|---|---|---|
| Teflon (FEP) | 2–3 | 1 | 2 |
| Polyester/Polyethylene | 2 | 1 | 2 |
| Polyester | 2 | 1 | 2 |
| Matalized Polyester | 1 | 1 | 1 |
| Nylon/Saran | 1 | 1 | 1 |
| Polyethylene | 1 | 1 | 1 |

LEGEND
1. Completely unacceptable. Material does not survive the test intact in a least 50% of the trials.
2. Acceptable. This material survives the test in 50% to 90% of the trials.
3. Highly Acceptable. This material survived the test in better than 90% of the trials.

As will be appreciated from the teachings herein, polyethylene and polyester are unacceptable from a performance standpoint, due to cracking of the test material and unacceptable levels of tissue damage. In contrast, the polyimide film, for example, demonstrates highly acceptable physical strength and resistance to the freeze-thaw cycle. Moreover, the polyimide film demonstrates acceptable transplant tissue protection. One example of a polyimide film useful for the invention described herein is Kapton®, which is commercially available. Other film materials which meet the above criteria will be equally useful for practicing the invention described herein. Kapton®'s durability during these tests shows a significant and unexpected advantage over all other materials tested. This is primarily due to its overall strength and ability to remain pliable and flexible at temperatures at least as low as −196° C. Furthermore, the superior insulating qualities which are exhibited by Kapton® greatly reduce physical damage (i.e. tissue cracking), which occurs during freezing and thawing. Such cracking reduces cellular viability and tissue integrity, rendering the tissue unimplantable. In addition, Kapton® film is chemically inert due in part to a laminated layer of Teflon (FEP).

When fabricating and assembling the envelope package 10, the innermost envelope 16 is sterile inside and out, and of course the tissue specimen 17 and medium 17a sealed within the innermost envelope is also sterile. The interior 26 of the intermediate envelope 14 also are sterilized before receiving the innermost envelope 16, assuring that the innermost envelope remains in a sterile environment. The outside of the intermediate envelope 14 is likewise sterilized before placing the intermediate envelope within the outermost envelope although, as discussed below, the outside of the intermediate envelope is treated as though non-sterile during subsequent opening of the envelope package 10.

The inside of the outermost envelope 12 is sterilized before the intermediate envelope 14 (containing the innermost envelope 16) is placed within the outermost envelope. The outermost envelope 12 is then sealed as discussed above, completely isolating the interior of the outermost envelope from contamination by bacteria or by the liquid nitrogen medium in which the envelope package 10 is subsequently stored.

Once the tissue specimen is fully enclosed within the envelope package 10, the packaged tissue is preserved by freezing and is then immersed in liquid nitrogen for preservation.

Opening of the envelope package 10 takes place with the following steps, to preserve the sterility of the innermost envelope 16 and the tissue specimen 17 contained within the innermost envelope. The entire envelope package 10 is removed from the cryogenic storage medium or shipping container (not shown), and is at least partially thawed by placing the envelope package into a warm water bath. This bath is not sterile but should be proximate to a sterile field, for example, in the operating room where the tissue speciment will be implanted in the recipient. Once the envelope package is immersed in the water bath for the desired time, the envelope package is removed and the exterior of the outermost envelope 12 is dried. The outermost envelope 12 is now opened by cutting away the envelope end portion 32, as illustrated in FIG. 3. This cutting operation is accomplished with any suitable implement, such as the scalpel 33 or scissors; the involvement preferably is sterile, although this is not a requirement for maintaining the sterility of the tissue sample within the innermost envelope 16.

Once the outermost envelope 12 is cut open, the intermediate envelope 14 is withdrawn by using sterile forceps 36 or the like, as illustrated in FIG. 3. Although the interior of the outermost envelope 12 and the exterior of the intermediate envelope 14 were previously sterilized, the exterior of the intermediate envelope is treated as though non-sterile in the opening of the envelope package 10. Thus, it is recognized that the outside of the intermediate envelope 14 may become contaminated as the intermediate envelope is pulled through the cut edge of the outermost envelope 12, and so removal of the intermediate envelope need not take place in a sterile field.

The outermost envelope 12 is discarded after the intermediate envelope 14 is removed. The peel-back seal 28 of the intermediate envelope 14 is now opened, using sterilized forceps or other implements to hole the lower layer 24 at the outermost corner 31 while simultaneously unpeeling the upper layer 25. The completely peeled-back intermediate envelope 14 is illustrated at 39 in FIG. 3. The peel-back opening procedure of the intermediate envelope 14 avoids contaminating the interior region 26 of the intermediate envelope or the innermost envelope 16 therein, irrespective of possible contamination on the outside of the intermediate envelope. Thus, the upper layer 25 of the intermediate envelope 14 is peeled back as illustrated at 39 to expose the innermost envelope 16, without subjecting the innermost envelope to contact with any portion of the outer surface of the intermediate envelope. The innermost envelope 16 is now grasped by fresh sterile forceps 37 or the like, and is removed as indicated at 41 to a sterile field without exposing the outside of the innermost envelope to contamination. The innermost envelope is then opened in the sterile field, for removal of the tissue specimen contained within the innermost envelope.

It will now be understood that the present envelope package maintains a tissue specimen isolated from bacterial contamination and from contact with liquid nitrogen or another storage medium. The outermost envelope 12 is made impermeable to liquid nitrogen, without regard to whether the immediate contents of the outermost envelope become contaminated upon removal. Even if the intermediate envelope is contaminated when removed from the outermost envelope, the intermediate envelope can be opened in a way that preserves sterility of the innermost envelope. The possibility of liquid nitrogen seeping through the welds in the peel-back seal of the intermediate envelope is eliminated, because the peel-back seal is protected by the nitrogen-impermeable outermost envelope. Moreover, use of the innermost envelope gives extra sterility protection, and sterility of the innermost envelope could be maintained for some time even if the outermost envelope ruptures. The resulting envelope package is more durable than previous packages for sterile tissue specimens, and is easier to handle in the hospital operating room.

Although preferred materials are disclosed for each envelope, those skilled in the art will understand that other materials can be substituted so long as each individual envelope maintains the requirements disclosed herein. Furthermore, the envelope materials must be sterilizable and must withstand cryogenic temperatures without undergoing significant degradation of physical qualities.

It should be understood that the foregoing relates only to a preferred embodiment of the present invention, and that numerous changes and modifications therein may be made without departing from the spirit and scope of the invention as defined in the following claims.

I claim:

1. A package for storage of a sterile transplantable specimen in a cryogenic atmosphere, comprising:

an outermost envelope having a non-sterile exterior, *said envelope made from a material* that provides an impermeable barrier to [the cryogenic atmosphere] *liquid nitrogen* and *said envelope* having closure means impenetrably sealed against [the cryogenic atmosphere] *liquid nitrogen* to define a closed sterile interior, an intermediate envelope removably received within the outer envelope and having at least two walls sealed to each other around the periphery thereof to define the closed interior, and an innermost envelope removably situated within the interior of the intermediate envelope comprised of at least two walls sealed to each other around the periphery thereof to define an inner, sterile cavity, wherein said outermost envelope protects against contact by [the cryogenic atmosphere] *liquid nitrogen*, and the intermediate envelope maintains the sterile exterior of the innermost envelope irrespective of possible contamination occurring to the exterior of the intermediate envelope during removal from the outer envelope, said package being in the cryopreserved state, *and wherein the outermost envelope and the innermost envelope are comprised of a material resistant to damage upon cryopreservation and thawing, and which is effective for protecting a transplantable tissue sample contained within the cavity of the innermost envelope from damage due to cryopreservation and thawing,*

*and further wherein the intermediate envelope comprises a peelback opening having a pair of surfaces defining the interior of the intermediate envelope and releasably bonded together along a predetermined course at the periphery of the interior; and the bond of the surfaces being selectively separable by peeling back one such surface relative to the other surface, thereby exposing the sterile interior of the intermediate envelope and the sterile innermost envelope received within, without subjecting the interior of the innermost envelope to possible contamination on the exterior of the intermediate envelope, so that the intermediate envelope is openable without subjecting the innermost envelope to possible contamination on the exterior of the intermediate envelope,*

*and further wherein the intermediate envelope comprises a peelback opening having a pair of surfaces defining the interior of the intermediate envelope and releasably bonded together along a predetermined course at the periphery of the interior; and the bond of the surfaces being selectively separable by peeling back one such surface relative to the other surface, thereby exposing the sterile interior of the intermediate envelope and the sterile innermost envelope received within, without subjecting the interior of the innermost envelope to possible contamination on the exterior of the intermediate envelope, so that the intermediate envelope is openable without subjecting the innermost envelope to possible contamination on the exterior of the intermediate envelope.*

[2. The package of claim 1 wherein the outermost envelope is comprised of a material resistant to damage upon cryopreservation and thawing, and which is effective for protecting a transplantable tissue sample contained within the cavity of the innermost envelope from damage due to cryopreservation and thawing.]

3. The package of claim 2 wherein the outermost envelope is comprised of polyimide.

4. The package of claim 3 wherein said polyimide is polyimide/fluorinated ethylene polypropylene laminate.

[5. The package of claim 1 wherein the innermost envelope is comprised of a material resistant to damage upon cryopreservation and thawing and which is effective for protecting a transplantable tissue contained within the innermost cavity from damage due to cryopreservation and thawing.]

6. The package of claim 5 wherein the innermost envelope is comprised of polyimide.

7. The package of claim 6 wherein said polyimide is polyimide/fluorinated ethylene polypropylene laminate.

8. The package of claim 1 in combination with a transplantable tissue contained within the innermost envelope.

* * * * *